United States Patent
Nugent et al.

(10) Patent No.: US 7,220,595 B2
(45) Date of Patent: May 22, 2007

(54) AUTOMATED IMMUNOASSAY CASSETTE, APPARATUS AND METHOD

(75) Inventors: Anthony J. Nugent, Dublin, CA (US); Leanne M. Cowley, San Jose, CA (US); Neal F. Bellet, Walnut Creek, CA (US); Jeffrey Shindelman, Castro Valley, CA (US); Michael E. Leos, Fairfield, CA (US); Thomas E. Worthy, Walnut Creek, CA (US); Kimberly Haley, Belmont, CA (US)

(73) Assignee: Cholestech Corporation, Hayward, CA (US)

( * ) Notice: Subject to any disclaimer, the term of this patent is extended or adjusted under 35 U.S.C. 154(b) by 698 days.

(21) Appl. No.: 10/456,230

(22) Filed: Jun. 6, 2003

(65) Prior Publication Data

US 2004/0029293 A1 Feb. 12, 2004

Related U.S. Application Data

(60) Provisional application No. 60/387,287, filed on Jun. 7, 2002.

(51) Int. Cl.
*G01N 33/558* (2006.01)

(52) U.S. Cl. ............... 436/514; 422/56; 422/57; 422/58; 435/287.2; 435/287.7; 435/287.9; 435/805; 435/810; 435/970; 436/518; 436/810

(58) Field of Classification Search ............. 422/56, 422/57, 58; 435/287.2, 287.7, 287.9, 805, 435/810, 970; 436/514, 518, 810
See application file for complete search history.

(56) References Cited

U.S. PATENT DOCUMENTS 4,313,734 A 2/1982 Leuvering (Continued)

FOREIGN PATENT DOCUMENTS

| WO | WO98/37416 | 8/1998 |
|----|------------|--------|
| WO | WO00/42434 | 7/2000 |

OTHER PUBLICATIONS

Kuller, L. H., et al., "Relation of C-reactive protein and coronary heart disease in the MRFIT nested case-control study. Multiple Risk Factor Intervention Trial," *Am J. Epidemiol.* (1996) 144(6):537-547 (abstract only).

(Continued)

*Primary Examiner*—Christopher L. Chin
(74) *Attorney, Agent, or Firm*—Jacqueline F. Mahoney; Lee Ann Gorthey; Perkins Coie LLP

(57) ABSTRACT

An immunoassay cassette, apparatus, and method for detecting an analyte in a liquid body-fluid sample are disclosed. The cassette has a body and a support mounted on the body, for movement toward and away from a sample transfer position. Sample supplied to a sample well in the cassette body is taken up by a reagent reservoir containing a first reagent composition effective to form a modified sample. The support provides a reagent strip having a transfer zone that is brought into contact with the reservoir, when the support is in the transfer position, a detection zone located downstream of the transfer zone, and a second reagent composition effective to react with the modified sample to form a detectable analyte-dependent product. By controlling movement of the support, volume and rate of sample flow from the reservoir to the strip can be controlled to optimize and/or standardize sample-transfer conditions in the assay.

21 Claims, 5 Drawing Sheets

U.S. PATENT DOCUMENTS

| | | |
|---|---|---|
| 4,552,839 A | 11/1985 | Gould et al. |
| 4,632,901 A | 12/1986 | Valkirs et al. |
| 4,743,560 A | 5/1988 | Campbell et al. |
| 4,756,828 A | 7/1988 | Litman et al. |
| 4,816,224 A | 3/1989 | Vogel et al. |
| 4,920,046 A | 4/1990 | McFarland et al. |
| 4,943,522 A | 7/1990 | Eisinger et al. |
| 4,956,275 A | 9/1990 | Zuk et al. |
| 4,959,324 A * | 9/1990 | Ramel et al. ............... 436/169 |
| 4,963,468 A | 10/1990 | Olson |
| 4,981,786 A | 1/1991 | Dafforn et al. |
| 4,999,285 A | 3/1991 | Stiso |
| 5,075,078 A | 12/1991 | Osikowicz et al. |
| 5,110,724 A | 5/1992 | Hewett |
| 5,135,873 A | 8/1992 | Becker et al. |
| 5,137,808 A | 8/1992 | Ullman et al. |
| 5,171,688 A | 12/1992 | Hewett et al. |
| 5,252,496 A | 10/1993 | Kang et al. |
| 5,260,221 A * | 11/1993 | Ramel et al. ............... 436/169 |
| 5,559,041 A | 9/1996 | Kang et al. |
| 5,591,645 A | 1/1997 | Rosenstein |
| 5,591,646 A | 1/1997 | Hudson et al. |
| 5,611,995 A | 3/1997 | Groothuizen et al. |
| 5,622,871 A | 4/1997 | May et al. |
| 5,654,162 A | 8/1997 | Guire et al. |
| 5,656,503 A | 8/1997 | May et al. |
| 5,714,389 A | 2/1998 | Charlton et al. |
| 5,744,096 A | 4/1998 | Barr et al. |
| 5,989,921 A | 11/1999 | Charlton et al. |
| 6,027,943 A | 2/2000 | Kang et al. |
| 6,187,598 B1 | 2/2001 | May et al. |
| 6,194,225 B1 | 2/2001 | Oka et al. |
| 6,228,660 B1 | 5/2001 | May et al. |
| RE37,437 E | 11/2001 | Friesen et al. |
| 6,352,862 B1 | 3/2002 | Davis et al. |
| 6,406,920 B1 | 6/2002 | Davis et al. |

OTHER PUBLICATIONS

Mendall, M.A., et al, "C reactive protein and its relation to cardiovascular risk factors: a population based cross sectional study," *BMJ* (1996) 312(7038):1061-1065 (abstract only).

Chandler, et al., *IVD Technology*, 6(2):37-49 (2000).

De Maat, et al., *Fibrinolysis*, 8(Suppl 2):50-52 (1994).

Grau, et al., *Stroke*, 26(9):1520-1526 (1995).

Kuller, et al, *Am J. Epidemiol.* 144(6):537-547 (1996).

Liuzzo, et al., *N. Engl J. Med.*, 331(7):417-424 (1994).

Mendall, et al, *BMJ* 312(7038):1061-1065 (1996).

Thompson, et al., *N. Engl J. Med.*, 332(7):635-641 (1995).

Tracy, et al., *Circulation*, 93(3):8 (1996).

* cited by examiner

AUTOMATED IMMUNOASSAY CASSETTE, APPARATUS AND METHOD

This application claims benefit of the priority of U.S. Provisional application Ser. No. 60/387,287, filed Jun. 7, 2002, which is incorporated herein in its entirety.

FIELD OF THE INVENTION

The present invention is directed to a cassette, apparatus and method for use in assaying a body fluid sample for a selected analyte, and particularly for use in automated multi-stage assays.

REFERENCES

De Maat, M. P. M. et al., *Fibrinolysis* 8(Suppl 2):50–52 (1994).
Grau, A. J. et al., "Clinical and Biochemical Analysis in Infection-Associated Stroke." Stroke 26(9):1520–1526 (1995).
Harlow, E. et al., "Antibodies: A Laboratory Manual", Cold Spring Harbor Lab (1988).
Hewett, G. E., U.S. Pat. No. 5,110,724 (1992).
Hewett, G. E. et al., U.S. Pat. No. 5,171,688 (1992).
Kuller, L. H. et al., *Am J Epidemiol.* 144:537–5547 (1996).
Leuvering et al., U.S. Pat. No. 4,313,734 (1982).
Liuzzo G, M. D. et al., *N Engl J Med* 331 (7):417–424 (1994).
Mendall, M. A. et al., *British Med. J.* 312:1061–1065 (1996).
Thompson, S. G. et al., *N Engl J Med* 332:635–641 (1995).
Tracy, R. P. et al., *Circulation,* 93(3):8 (1996).

BACKGROUND OF THE INVENTION

Assays for detecting the presence and level of a variety of analytes in body fluid samples are known. Such assays are often designed for simplicity of use so that they can be reliably conducted in a doctors office or other clinical setting where personnel may have little training in clinical assay procedure or in interpreting assay results. In order to minimize the need for operator involvement, it is preferable that the assay be carried out in an automated or self-contained manner.

Such self-contained assays have typically been limited, for the sake of simplicity of operation, to one-step assay procedures. A number of useful assays, however, are multistage in nature, requiring more than one reacting or binding step. Further, one or more of the steps may be rate limiting, or affected by localized reagent concentrations. Typically, multistage assays are less readily automated and generally require more input from the user, thus increasing the possibility of error.

It is therefore desirable to provide an automated, self-contained assay device which is able to perform multistage assays, in particular those containing multiple reacting or binding steps in which one or more of the steps is rate limiting or the final assay result is affected by localized reagent of analyte concentrations.

SUMMARY OF THE INVENTION

In one aspect, the invention includes an immunoassay cassette for use in detecting an analyte in a liquid body-fluid sample is disclosed. The cassette provides a cassette body having a sample well for receiving the sample, a support mounted on the body, for movement toward and away from a transfer position, and a reagent reservoir and a reagent strip carried on the body and support, respectively. The reagent reservoir contains a first reagent composition effective to react with one or more sample components to form a modified sample, as sample migrates from the sample well into the reservoir. The reagent strip contains a second reagent composition effective to react with the modified sample to form a detectable analyte-dependent product. The reagent strip has a transfer zone that is brought into contact with the reservoir, when the support is moved to its transfer position, and a detection zone located downstream of the transfer zone. By controlling the movement of the support toward and away from its transfer position, the volume and rate of sample flow from the reservoir to the strip can be controlled to optimize and/or standardize sample-transfer conditions in the assay.

For use in detecting a multivalent analyte in a liquid body-fluid sample, the first reagent composition in the reagent reservoir may include a non-immobilized conjugate of an anti-analyte antibody and a detectable reporter group, where the reaction to form a modified sample includes binding of the conjugate to sample analyte, to form an analyte-conjugate complex. The second reagent composition in the reagent strip may include an anti-analyte antibody immobilized at a detection region in the reagent strip located downstream of the strip's sample-transfer region, where the reaction to form a detectable analyte-dependent product includes binding of complex to the immobilized antibody, to localize the detectable reporter in the complex at the detection zone. The nonimmobilized conjugate in this embodiment may be a conjugate of an anti-analyte-antibody and a visible reporter, such as metal particles, particles labeled with colored or fluorescent moieties, polymers labeled with colored or fluorescent moieties, particles, or colored or fluorescent molecules.

For use in detecting C-reactive protein analyte in a blood sample, the anti-analyte antibody in the non-immobilized conjugate in the reagent reservoir, and the immobilized anti-analyte antibody in the reagent strip may be antibodies specific against a common epitope in C-reactive protein. Alternatively, the two antibodies may be directed against different C-reactive protein epitopes.

The support may include a window through which binding of the complex at the detection zone in the reagent strip can be viewed. In addition, the detection zone in the reagent strip may be covered by a reflective film at the strip surface facing away from the window.

The cassette may further include an absorbent reservoir carried on the support, downstream of said detection zone, for receiving sample liquid transferred through the reagent strip.

In another aspect, the invention includes apparatus for use in detecting an analyte in a liquid body-fluid sample. The apparatus includes a cassette of the type described above, and a cassette-handling instrument. The instrument has (a) a cassette holder into which the cassette is removably placed, during a sample assay, (b) an actuator operable to move the support in the cassette toward and away from its sample-transfer position, (c) a detector operable to detect an analyte-specific reaction at the detection zone in the reagent strip, and (d) a processor operably connected to the actuator, for controlling the volume timing and rate of movement of sample material from the reagent reservoir to the reagent strip.

In one embodiment, the detection zone in the reagent strip in the cassette is covered by a reflective film at the strip's surface facing away from said window, such that flow of sample liquid through the detection zone produces a first change in reflectance measurable through the window, and the presence of analyte-dependent reaction at the detection zone produces a second change in reflectance measurable through the window. The detector may be operable to detect liquid flow through the detection zone, by a first change in measured optical reflectance, and is operable to measure a subsequent analyte-dependent reaction at the detection zone, by a second change in measured optical reflectance.

The control unit may be operable to control the volume and rate of sample transfer from the reagent reservoir to the reagent strip by controlling one or more of (i) the period of sample incubation before sample is first transferred from the reservoir to the reagent strip, (ii) the cycle frequency with which the actuator moves the support toward and away from its transfer position, (iii) the time of contact that the support is held in its transfer position, during each cycle, and (iv) the total number of transfer cycles. Preferably, the unit is operable to control the volume and rate of sample transfer from said reservoir to the reagent strip by controlling (i) the cycle frequency with which the actuator moves the support toward and away from its transfer position and (ii) the time of contact that the support is held in its transfer position, during each cycle.

In still another aspect, the invention includes a method of conducting an assay for a body-fluid analyte, by the steps of: (a) introducing a body fluid containing the analyte into a absorbent reservoir containing a first reagent composition effective to react with one or more sample components to form a modified sample, (b) repeatedly contacting the reservoir, with such containing an absorbed body-fluid sample, with an absorbent reagent pad containing a second reagent composition effective to react with the modified sample formed in the reservoir to produce a detectable analyte-dependent product, and (c)controlling the frequency and duration of said contacting, thereby to control the volume and rate of transfer of sample fluid from the reservoir to the pad.

In one general embodiment, the reagent pad is an elongate reagent strip having a sample-transfer zone at which the reservoir makes contact with the strip, and a detection zone located downstream of the transfer zone.

For detecting a multivalent analyte in a liquid body-fluid sample, such as C-reactive protein in a blood or serum sample, the first reagent composition in the reagent reservoir may include a non-immobilized conjugate of an anti-analyte antibody and a detectable reporter group, and the reagent composition in the reagent strip, an anti-analyte antibody immobilized at a detection region in the reagent strip.

These and other objects and features of the invention will become more fully apparent when the following detailed description of the invention is read in conjunction with the accompanying drawings.

DETAILED DESCRIPTION OF THE INVENTION

I. Immunoassay Cassette

For convenience, similar element numbering is retained in all the figures to identify like structural features.

Figure 1A:
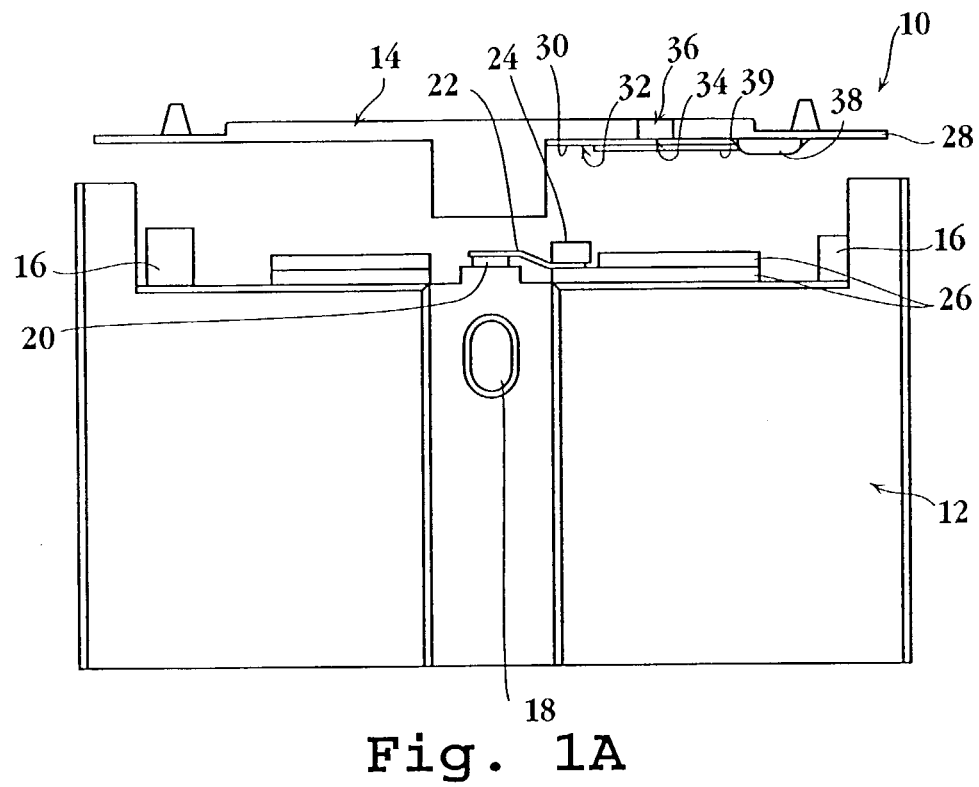
FIGS. 1A and 1B are plan views of an immunoassay cassette constructed in accordance with one embodiment of the invention, with the cassette in an initial sample loading position (FIG. 1A), and a sample-transfer position (FIG. 1B)
Figure 1B:
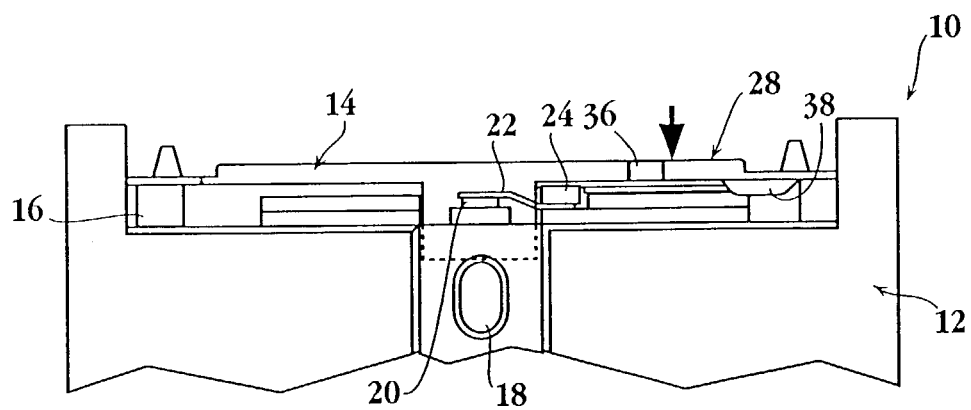

FIGS. 1A and 1B show an immunoassay cassette 10 constructed according to one embodiment of the invention. The cassette contains two plate-like members, a base member or body 12 and a support or support member 14, which may be produced by standard molding or machining methods. The support is mounted on the body for movement in a vertical direction in the figures from an at-rest position seen in FIG. 1A to a sample-transfer position shown in FIG. 1B. More particularly, the support is mounted for movement toward and away from a sample transfer position.

The structure mounting the support on the body may be compressible blocks, such as elastomeric blocks, as shown at 16, which support opposite ends of the support. These blocks become compressed as the support is moved from its at-rest position, where the blocks are substantially uncompressed, to the sample-transfer position, where the blocks are maximally compressed. It will be appreciated that a variety of compressible structures, such as springs or magnets, could be to mount the support on the cassette body for biased movement toward and away from the sample-transfer position.

Provided within body 12 is a sample well 18 for receiving the body fluid sample to be analyzed. The well is designed to receive a body-fluid sample, such as a blood or serum sample, typically having a volume between about 20 and about 60 µl. The sample well transfers sample to a center pad 20. The center pad, in turn, communicates through a capillary wick 22, also referred to herein as a spreading layer, with a reagent pad or reservoir 24 containing a first reagent or reagent composition, to be described. When sample liquid is placed in well 18, it migrates by capillarity through the center pad, and from the center pad, through the spreading layer to the reservoir 24. Where the sample being analyzed is a blood sample, one of more of the elements in the flow path between the sample well and the reservoir, and typically the center pad and/or the spreading layer, may be effective to remove or retard the flow of red blood cells, so that the sample material reaching the reservoir has been freed of blood cells or other particulate components. Glass fiber and other matrix material suitable for this purpose are well known.

Alternatively, or in addition, one or more of the elements in the flow path may be effective to remove undesired sample components through the use of immobilized binding agents, e.g., antibodies, specific against the unwanted components. Undesired sample components can also be removed by exposing the sample to a precipitating agent in the flow path effective to selectively precipitate the undesired sample components. For example, dextran sulfate may be used to selectively precipitate certain lipoproteins in a blood sample. The precipitated particles are either blocked from migration through the flow path, or retarded in flow. The center pad, sample transfer strip, and reservoir are preferably formed of bibulous, fibrous material capable of drawing fluid via capillary flow. A variety of fibrous materials, such as are commonly used in fibrous-mat filters, including cellulose, cellulose acetate, and glass fibrous matrices, are suitable materials for the transfer strip. The fibers may be crosslinked, if desired, by chemical crosslinking, heat fusion, or the like. Also suitable are porous substrates, such as sintered glass, fused polymer beads, and the like, whose wettability and dimension of interstices are such as to promote movement of an aqueous medium into the strip by surface wetting. One exemplary material is a glass fiber filter having a packing density of about 0.2–0.5 $gm/cm^3$. The center glass, spreading layer and reservoir may be mounted on the body directly on the body or through a backing made of plastic or other inert support material.

Although the cassette embodiment shown is designed for a single assay, at the right side of the cassette in the figures, it will be appreciated that the cassette could be adapted for additional assay(s) at the left side of the cassette. Further, the additional assay may have the same fluid-flow format, or may have a different format, e.g., the center pad may communicate with an elongate reaction strip extending along the upper left edge region of the cassette body.

Completing the description of the cassette body, a pair of elastomeric blocks 26 on either side of the center pad serve to cushion and limit the movement of the support as it is moved toward its sample-transfer position.

Support 14 has a pair of elongate reaction bars, such as bar 28, extending outwardly from the center of the support, as seen in FIGS. 1A and 1B. An elongate reagent strip 30 is affixed to and extends along the lower, inward-facing surface of the support, as shown. The strip has an upstream sample-transfer zone 32 and a downstream detection zone 34 located directly below a window 36 formed in the support bar. As seen in FIG. 1B, movement of the support to its sample-transfer position, with compression of blocks 16, brings the sample-transfer zone into contact with the reagent reservoir on the cassette body, promoting capillary fluid flow from the reservoir to the reagent strip.

The reagent strip is formed of a material porous or fibrous material which promotes capillary flow therethrough. Preferred materials include porous, fused polymer or microporous polymer membranes, such as polysulfone, polypropylene, nylon, nitrocellulose, Teflon™, or polyvinylchloride microporous membranes. In the present case, nitrocellulose, such as is available from Sartorius, is particularly preferred, with such having length, width, and thickness dimensions between 5–20 mm, 1–5 mm, and 0.1–0.5 mm, respectively.

The downstream end of strip 30 is in contact with an absorbent pad 38 which functions as a reservoir to draw sample liquid supplied to the strip at the sample-transfer zone, and flowing in a downstream direction (to the right in the figures) into and through the detection zone. The pad is formed of a suitable absorbent material such as fibrous glass or cellulose. The absorbance volume of the pad is preferably at least half of the volume of the sample added, e.g., 10 to 30 µl.

Disposed within the fluid pathway defined by the reagent strip are reagents, described further below, effective to produce a detectable, analyte-dependent reaction product which is detected at the detection zone. Various assays may therefore be carried out using the cassette, as described below.

The outer-facing surface of the reagent strip, downstream of the sample-transfer zone, is covered by an impermeable reflective film 39, such as a Mylar film. In particular, the film extends over the detection zone in the reagent strip, which is sandwiched between the support window and the reflective film. The purpose of the reflective strip is to enhance the reflectivity of the reagent strip, as viewed through the support window, and in particular, to enhance the change in reflectivity observed when the strip is wetted, and in response to an analyte-specific reaction occurring in the detection zone, as will be discussed further below.

Figure 2:
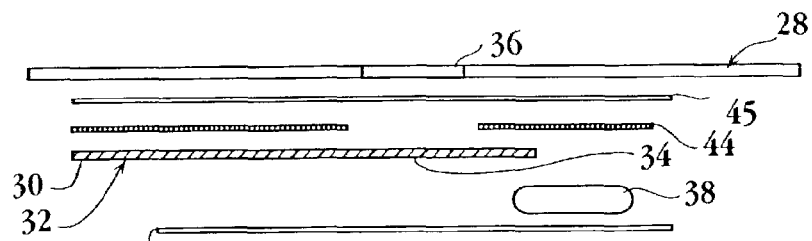
FIG. 2 is an enlarged section view of the cassette support in the region of the detection zone.

The construction of the various layers on the support is illustrated in exploded view in FIG. 2. Shown here are support bar 28 having window 36 located therein, and reagent strip 30 having upstream sample-transfer zone 32 and detection zone 34. The strip is attached to the support bar with a double-side adhesive strip 44 initially covered with a removable backing 45. As shown, the adhesive strip is separated by a space corresponding to the support window and detection zone. Absorbent pad 38 is positioned to overlap with the downstream end of reagent strip 30, and the reflective film is positioned to extend from a point just downstream of the sample-transfer region in strip 30 to a point beyond the absorbent pad. In construction, the components above are arranged as shown, and attached to the support bar and to one another by removing adhesive backing 44 and pressing the adhesive side of the assembly firmly against the support bar.

The cassette is designed particularly for an analyte assay in which (i) sample components, which typically include the analyte itself, react with one or more reagents in the reservoir to form a modified sample, and (ii) the modified sample, typically modified analyte, reacts with a second reagent composition to produce a detectable, analyte-dependent product. That is, both the reagent reservoir and the reagent strip in this preferred embodiment contain one or more reagents for carrying out these reactions. The one or more reagents in the reservoir and strip are also referred to herein as a first and second reagent compositions, respectively, and may include one or more enzymes, antibodies, labeled antibodies, or enzyme substrates, binding agents, and/or precipitation agents, as discussed further below.

In one exemplary cassette, for detection of a multi-valent antigen analyte, the reagent composition in the reservoir includes a non-immobilized analyte-specific antibody labeled, e.g., covalently with a detectable reporter, e.g., metal particles, fluorescent or colored molecules, branched polymers containing attached colored or fluorescent moieties, and coated particles, e.g., fluorescent-coated latex particles. By "non-immobilized" is meant that the reagent is freely mobile within the reservoir. Thus, when analyte is added to the reservoir, it reacts specifically with the antibody reagent to form a mobile, labeled analyte-antibody complex. In other embodiments, the reagent compositions may be immobilized or non-immobilized, depending on whether the reagent must co-migrate with the analyte and/or whether the reagent would be expected to interfere with the final analyte determination.

Methods of labeling a binding agents, such as labeled antibodies, are known in the art, including the use of radiolabels, fluorescent labels, or linked enzymes which convert a separate substrate to a detectable species. A variety of reporter-labeled antibodies, such as enzyme-labeled antibodies, are commercially available or may be readily prepared according to known methods (see, e.g., Harlow, pp. 319–358). Optically detectable labeling methods are preferred for use with the present immunoassay cassette. Enzymes which react with a substrate to produce a visible reaction product are widely used for this purpose. A particularly preferred labeled reagent is an analyte-specific antibody conjugated to a visible particle such as a colored latex bead or colloidal gold. Such conjugates are described in U.S. Pat. No. 4,313,734 (Leuvering) and may also be obtained from manufacturers such as BB International (Cardiff, UK) and NanoProbes (Stony Brook, N.Y.).

The reagent composition in the reagent strip, which may include one or more reagents, may be distributed throughout the strip, or localized on the strip, for example, at the sample-transfer zone, just downstream of the transfer zone, or in the detection zone, in immobilized or non-immobilized form. In the embodiment described above, for detection of a multivalent analyte, the second reagent composition includes an anti-analyte antibody immobilized at the detection zone. In this format, labeled analyte-antibody complex transferred from the reservoir to the reagent strip migrates in a downstream direction in the strip, where it is captured in the detection zone. The step of forming a detectable reaction product includes capturing a detectable complex at the detection zone.

In other embodiments, the second reagent composition may include immobilized or non-immobilized enzymes, substrates, labeled binding reagents, photosensitizer agents, reducing or oxidizing agents, and/or acid or base groups that that can donate protein and hydroxyl ions as part of an analyte-detection reaction, according to known, two-step reaction procedures, where, in the present invention, one of the steps is to be carried out in the reagent reservoir, and the second in the reagent strip.

More specifically, the detection zone may contain reagents effective to produce a detectable reaction product with unlabeled antibody-analyte complex. For example, the detection zone may contain an oxidase, a peroxidase, and a compound oxidizable to a detectable species such as a dye. When the analyte-antibody complex includes a substrate for the oxidase, the $H_2O_2$ generated in the resulting reaction reacts with the oxidizable compound, catalyzed by the peroxidase, to generate the detectable dye. Such assays are described, for example, in Hewett et al.

The reagents may be incorporated into the reservoir and strip by soaking the reservoir or strip material in a solution of the reagents, followed by drying, or adding a solution of the reagent material to the entire or a localized region of the strip, followed by drying. Where the reagent is immobilized, the reservoir or strip region may naturally provide, or be chemically modified according to known methods to have surface reactive groups, such as amine, carboxyl, sulfhydryl, or aldehyde groups, allowing covalent coupling by the use of activating agents or bifunctional coupling agents.

In one particular embodiment, the cassette is designed for detection of C-reactive protein, typically measured in a blood or serum sample. In this embodiment, the reagent composition in the reservoir is a non-immobilized monoclonal antibody specific against a C-reactive protein epitope, i.e., an epitope on one of the 5 identical subunits in C-reactive protein. One exemplary anti-C-reactive protein antibody is a monoclonal antibody produced by cell line identified by clone number CC002, and available from Scripps Laboratories (San Diego, Calif.). The antibody is labeled by conjugation to gold microparticles, according standard methods, e.g., as described in, Chandler, et al., The place of gold in rapid tests, *IVD Technology*, 6(2)37–49 (2000). The second reagent is an antibody specific against C-reactive protein and immobilized at the detection zone. An exemplary antibody is the same as that employed in the first (reservoir) antibody reagent. Details of the assay are given in Example 1.

Figure 3A:
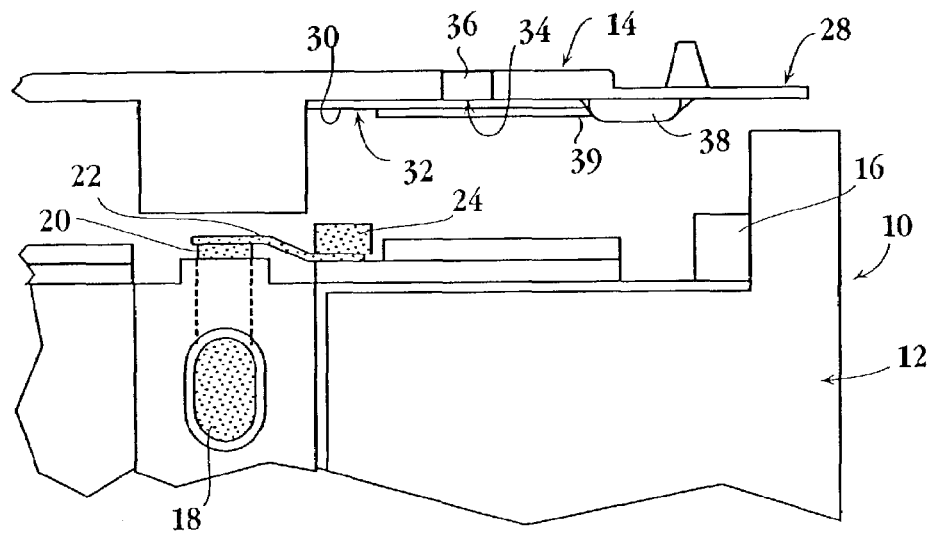
FIGS. 3A and 3B illustrate the distribution of sample fluid prior to (FIG. 3A), and following (FIG. 3B) sample-fluid transfer in the cassette.
Figure 3B:
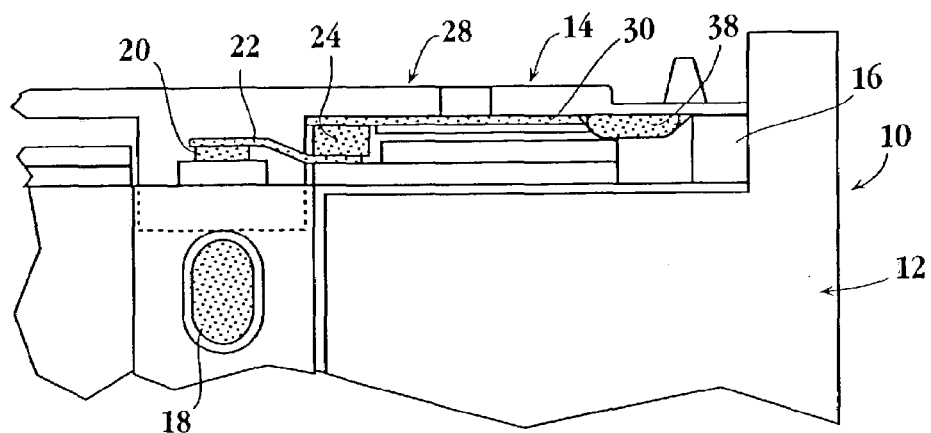

FIGS. 3A and 3B illustrate the flow of sample liquid into and through the fluid-flow elements of the cassette during cassette operation. As seen in FIG. 3A, liquid sample applied to sample well 18 is drawn by capillarity into center pad 20, and from here, through the spreading layer into reservoir 24. Here the sample may be held for a desired incubation time, in the presence of the first reagent. Typical incubation times may vary from a few seconds up to ten minutes or more.

When the support in the cassette is moved to its sample-transfer position, shown in FIG. 3B, sample liquid flows by capillarity into the strip transfer zone when the latter is brought into contact with the reservoir. From the transfer zone, the sample liquid migrates in a downstream direction into and through the detection zone and ultimately into absorbent pad 38. By controlling the delay between addition of sample material to the cassette sample well and initial movement of the support to its sample-transfer position, the cassette can be operated to control the period of sample incubation before sample is first transferred from the reservoir to the reagent strip.

In addition the rate of liquid transfer, and the total sample volume transferred can be controlled by controlling (i) the cycle frequency with which the actuator moves the support toward and away from its transfer position, (ii) the time of contact that the support is held in its transfer position, during each cycle, and (iii) the total number of transfer cycles. As discussed in the next section, this control is conveniently provided by a cassette-handling instrument in an assay apparatus constructed in accordance with another aspect of the invention.

II. Cassette-handling Instrument

Figure 4:
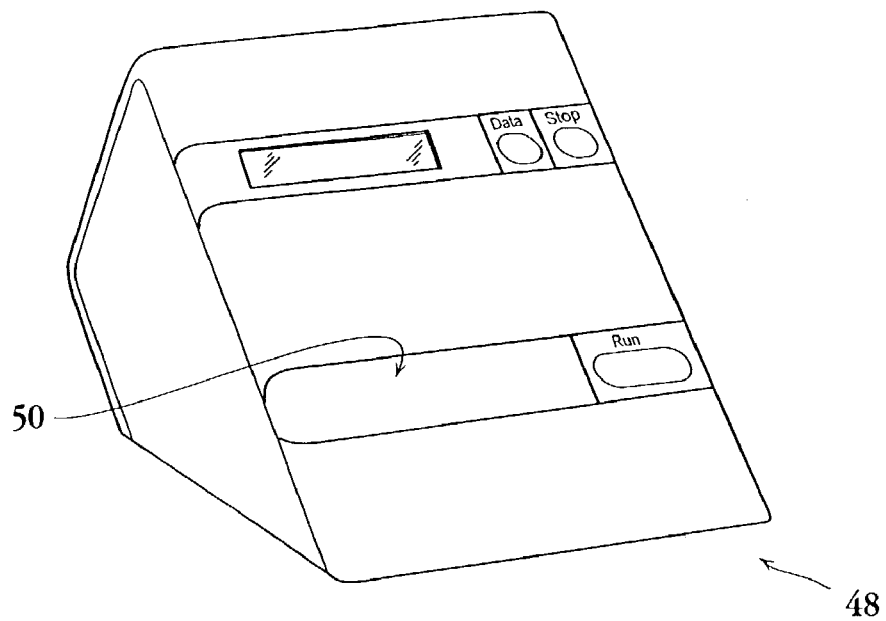
FIG. 4 is a perspective view of a cassette-handling instrument constructed according to one embodiment of the invention.
Figure 5:
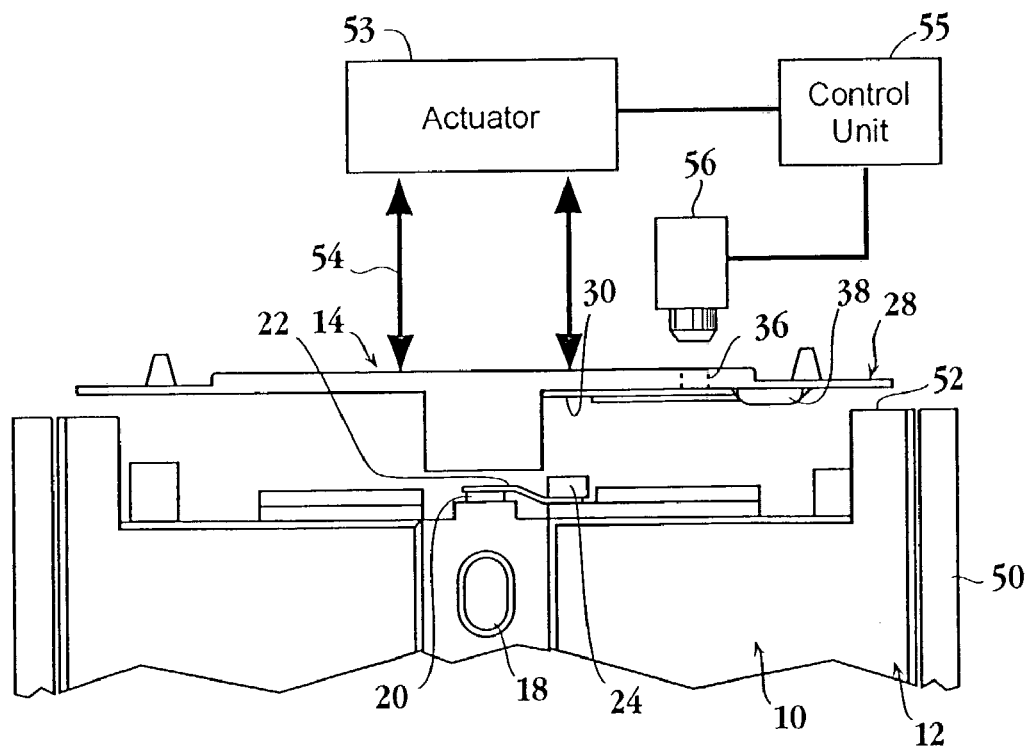
FIG. 5 illustrates various functional components of the cassette-handling instrument in relationship to an immunoassay cassette of the invention.

FIG. 4 is a perspective view of a cassette-handling instrument 48 constructed in accordance with the invention, and FIG. 5 shows key functional elements of the instrument in diagrammatic form. The instrument includes a cassette holder, represented by arms 50, adapted to receive and hold the cassette in an operative condition when a sample liquid has been added to the cassette. In particular, arms 50 are biased to engage guide notches, such as notches 52, in the cassette body to anchor the cassette in the holder at a desired position.

The instrument further includes an actuator 53 having solenoid-activated pistons or pushers, indicated at 54 operable to engage the cassette support and move the support from its relaxed-state to its sample-transfer position, upon actuation from a control unit 55 in the instrument. In particular, the control unit may be programmed or user-adjusted to control the one or more of the following actuator variables:

(i) the period between sample addition to the cassette sample transfer to the strip. This time corresponds roughly to the incubation period of sample liquid exposure to and reaction with the first reagent composition, and may vary from several seconds up to 10 minutes or longer, depending on the nature of the first sample reaction.

(ii) the cycle frequency with which the actuator moves the support toward and away from its transfer position. The frequency may be varied between one per assay, to a few per minute to one per second.

(iii) the time of contact that the support is held in its transfer position, during each cycle. Together with frequency, this variable determines the total rate at which sample fluid is transferred to the reagent strip. This rate can be optimized for different types of assay chemistries. For example, it may be desirable to regulate the flow of material from the sample well through the reagent reservoir, to ensure sufficient reaction time in the reagent reservoir, or to meter the flow rate through the reagent strip, to ensure adequate reaction time in the strip.

(iv). the total number of transfer cycles, which, together with contact time in each cycle, will determine the total volume transferred from the cassette body to the strip. By controlling the total volume transferred, a more quantitative measure of analyte concentration, expressed as amount of analyte/volume of sample can be determined. In particular, the volume that passes through the detection zone will be the total amount transferred less a predetermined quantity remaining in the portion of the strip upstream of the detection zone.

It will be appreciated that the control unit can be preprogrammed to control liquid transfer in the assay in an optimized manner for any selected type of assay chemistry. Various liquid transfer profiles that can be achieved with the invention will be considered below.

Also as shown in FIG. 5, the cassette-handling instrument includes a photo-detector 56, operable to detect changes in the reflectance of the detection zone, as observed through window 36. The photo-detector in this case may be a simple device for measuring the light intensity of reflectance at the window, when the detection window is illuminated by a light source, e.g., an LED, also forming part of the detector. In other embodiments, the detector may include a selected-wavelength fluorescence excitation beam and emitted-light detector, or a selected-wavelength visible light source and photo-detector for measuring light absorption at the detection surface.

Particularly where the light detector is designed to measure reflectance from the reagent strip surface in the detection zone, the reflective film is effective to enhance, i.e., amplify the reflectance intensity, and thus improve resolution and accuracy. As will be seen in the next section, the enhanced reflectance also allows the detection zone to serve as a "control" to monitor fluid flow through the reagent strip.

III. Performance Characteristics

As noted above, one feature of the invention is the ability to control the rate and volume of fluid flow from one reaction area to another, and thus the kinetics of the reactions and the total assay volume. This feature is important where one or more of the assay reactions are rate-limiting or where it is desired to assay a kinetic end point. The feature is also important in controlling the total amount of sample liquid that flows into and through the detection zone, for quantitating the concentration of analyte in the zone.

Figure 6A:
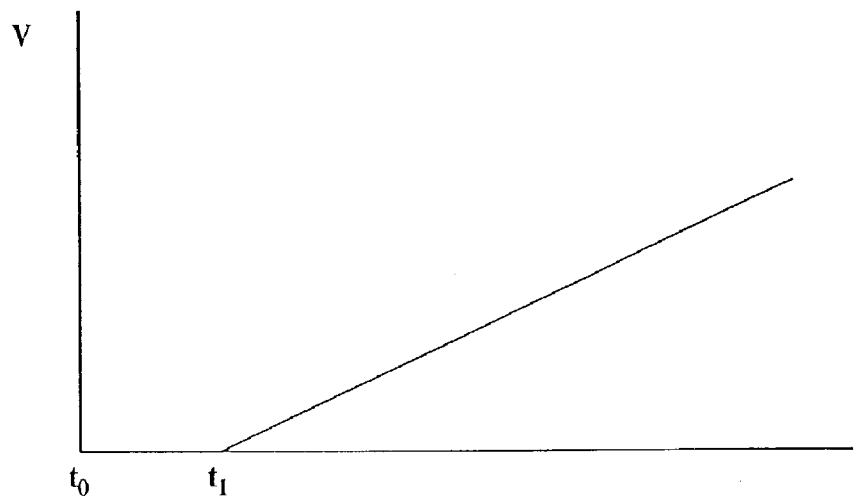
FIGS. 6A and 6B illustrate different sample-volume transfer profiles achievable by the invention.
Figure 6B:
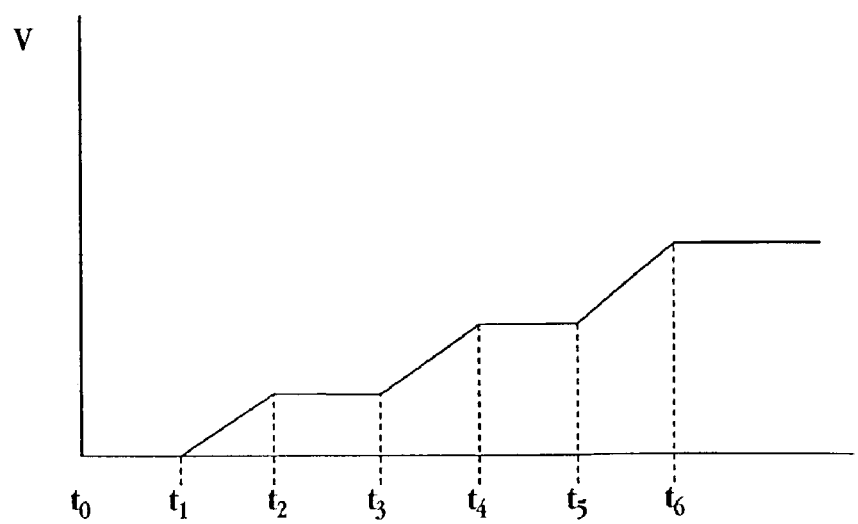

FIGS. 6A and 6B illustrate two sample transfer curves that illustrate the different sample transfer characteristics that can be achieved in the invention. In the first case, illustrated in FIG. 6A, sample is added to the cassette at time $t_0$, and allowed to incubate in the reagent reservoir until a time $t_1$, when the support bar in the cassette is brought into contact with the reservoir. If the support bar is held in contact with the reservoir over an extended period, sample transfer into the strip, expressed as sample volume as a function of time, increases linearly until a time $t_f$ when both strip and pad are fully saturated (ignoring sample evaporative effects).

In FIG. 6B, the sample incubation time, from $t_0$ to $t_1$, is the same as in FIG. 6A, but sample transfer is effected by three discrete transfer events, interspersed with intervals in which the support is move out of contact with the reservoir and volume accumulation over time is flat. As can be appreciated, the latter approach allows a more controlled, and typically slower rate of volume transfer than when sample transfer occurs as an unbroken event.

Figure 7:
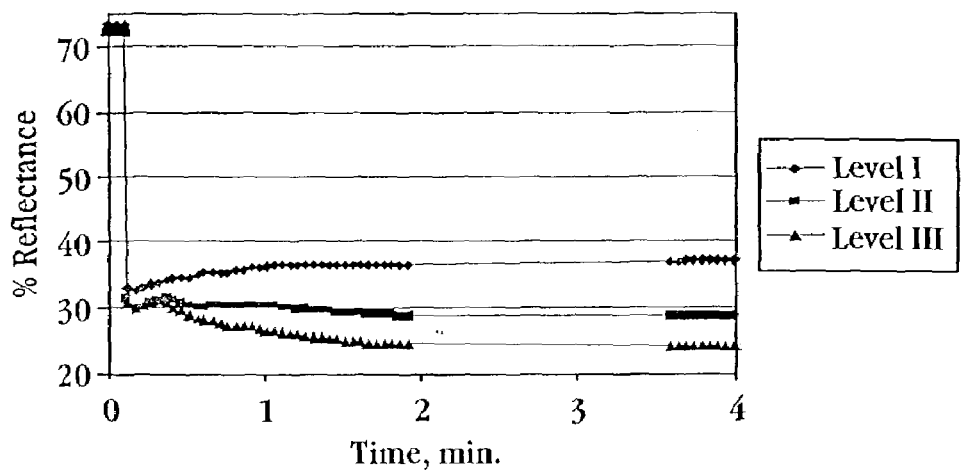
FIG. 7 illustrates reflectance profiles for a C-reactive protein analyte at three different concentrations, during an assay procedure in accordance with one embodiment of the invention.

FIG. 7 shows an exemplary reflectance curve for an assay in which C-reactive protein analyte reacts first with labeled anti-analyte antibody in the cassette reservoir, to form a detectable analyte-antibody complex, and the complex is then transferred to the reagent strip, where it is captured by an immobilized anti-analyte antibody in the detection zone. The initial reflectance, in the first few seconds after sample transfer to the support, corresponds to a dry strip reflectance. The precipitous drop in reflectance occurs when the leading edge of the transferred sample passes through the detection zone. The drop in reflectance is due both to the wetting of the strip in the detection zone and the presence of colloidal gold labeled antibodies, either in complexes or non-complexed form.

With continued flow of sample material through the detection zone, the level of reflectance begins to change over time, depending on the relative concentrations of complexed and non-complexed antibody conjugate, i.e., depending on the sample analyte concentration. At lower analyte concentration, where relatively more of the conjugate is in non-complexed form, and relatively less of the conjugate is captured at the detection zone, the reflectance begins to increase over time as more and more of the conjugate is carried out of the detection zone by sample transfer through the zone. This is seen in the "diamond" plot in FIG. 7. Conversely, at higher analyte concentrations, progressively more conjugate is captured in the detection zone, with sample flow through the zone, acting to decrease reflectance over time, as indicated for the "triangle" plot in the same figure.

The analyte concentration is measured by comparing the measured reflectance at a selected end point, e.g., 4 minutes, with standard reflectance measurements from known analyte concentrations. The measured reflectance may be expressed, for example, as a ratio of the final percent reflectance to initial percent reflectance. As seen in the plot shown in FIG. 8, a plot of this ratio shows an analyte-dependent curve over a C-reactive protein concentration of 0 to 8 μg/ml.

From the foregoing, it can be appreciated how various objects and features of the invention are achieved. The cassette provides a dry-strip assay format in which successive analyte-dependent reactions can be carried out in a controlled manner, by controlling volume and rate transfer from one reaction region to another. In addition, the cassette is designed to allow controlled and measured volumes of sample through the detection zone, for more quantitative determination of analyte concentration. The cassette format is amenable to multiple assays in the same cassette, and fed from the same sample. Finally, the reflector strip in the support bar acts to enhance reflectance changes, enhancing the reliability and resolution of an assay.

Preferably, the cassette of the invention is supplied with solutions and reagents preloaded and is thus entirely self-contained, not requiring operator loading of solutions. The reader containing the cassette may be programmed to adjust the cassette to its different operational positions at desig-

IV. EXAMPLES

Example 1

Assay for C-Reactive Protein

In a specific application of the present device, a blood sample was analyzed for levels of C-reactive protein. Altered levels of this compound have been shown to be diagnostic of disorders characterized by risk factors for cerebral vascular ischemia and stroke, and ischemic heart disease and stroke (see, for example, De Maat, Grau, Kuller, Liuzzo, Mendall, Thompson, and Tracy).

The assay was prepared as follows: The center pad was a glass fiber pad capable of absorbing about 20 µl of liquid. The spreading layer was also glass fiber. The reservoir was a porous plastic material having a total absorption volume of about 6 µl. The reservoir was initially soaked with 6 µl of a 20 O.D. solution of antibody conjugate formed by conjugating colloidal gold with antibody specific against C-reactive protein, obtained from BBInternational (Cardiff, UK). The reservoir was then dried.

The reagent strip in the cassette was an 11 mm by 3 mm nitrocellulose strip, obtained from Sartorius (Goettingen, GmbH), having a thickness of less than 10 mils (0.25 mm). The antibody against C-reactive protein was attached to the detection region through hydrophobic interaction with the nitrocellulose. The detection region was located about 6 mm from the sample-transfer region. The absorption pad at the downstream end of the strip was a cellulose fiber material, having a total absorption volume of about 25 µl.

Figure 8:
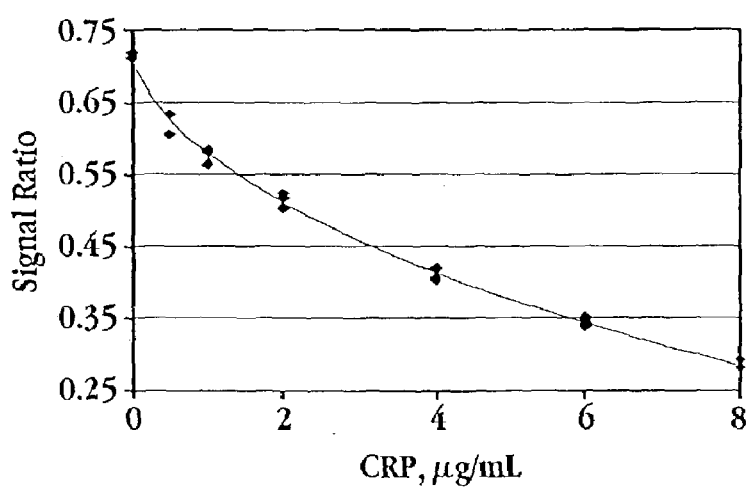
FIG. 8 is a plot of measured reflectance as a function of C-reactive protein analyte concentration, generated in accordance with the invention.

In the assay method, a 50 µl human blood sample was applied to the sample well in the cassette. After an incubation period of 3 minutes, the support was moved to its sample-transfer position for 4 minutes. During flow of sample liquid onto the strip, the reflectance at the support-bar window was monitored. At about 4 minutes, a stable end point was reached (FIG. 8). The signal ratio of end-point reflectance to initial reflectance was determined and used to calculate analyte concentration from a standard curve generated by samples with known amounts of C-reactive protein.

Example 2

Apparatus for Use with Assay Cassette

A cassette is prepared substantially as described in Example 1. The cassette is removably placed in a cassette holder during the sample assay. The cassette is moved toward and away from the sample-transfer position by an actuator to effect incubation of the reagents. The analyte-specific reaction in the detection zone of the reagent strip is detected by a detector. The volume and rate of sample transfer from said reagent reservoir to the reagent strip during the assay procedure is controlled by a control unit connected to the actuator.

Example 3

Analyte Assay

A body fluid suspected of containing the analyte of interest is introduced into an absorbent reservoir containing a reagent composition effective to react with one or more sample components to form a modified sample. The absorbent reservoir containing the absorbed body-fluid sample is repeatedly contacted with a reagent strip containing a second reagent composition effective to react with the modified sample formed in the reservoir to produce a detectable analyte-dependent product. The frequency and duration of the repeated contact are controlled to control the volume and rate of transfer of sample fluid from the reservoir to the pad. The analyte-dependent product is detected by any known means.

While the invention has been described with reference to specific methods and embodiments, it will be appreciated that various modifications may be made without departing from the invention.

It is claimed:

1. An immunoassay cassette for use in detecting an analyte in a liquid body fluid sample, comprising:
   (a) a cassette body having a sample well for receiving said sample;
   (b) carried on said body, (i) a reservoir containing a first reagent composition effective to react with one or more sample components to form a modified sample, when sample migrates from the sample well into the reservoir;
   (c) a support mounted on said body, for movement toward and away from a transfer position; and
   (d) carried on said support, a reagent strip containing a second reagent composition effective to react with the modified sample formed in said reservoir to form a detectable analyte-dependent product, said strip having a transfer zone which is brought into contact with said reagent reservoir, when the support is moved to its sample-transfer position, and a detection zone located downstream of the transfer zone,
   wherein controlled movement of said support toward and away from its transfer position is effective to meter the volume and rate of sample flow from the reservoir to the reagent strip.

2. The cassette of claim 1, for detecting a multivalent analyte in a liquid body-fluid sample, wherein the first reagent composition in the reagent reservoir includes a non-immobilized conjugate of an anti-analyte antibody and a detectable reporter group, the reaction to form a modified sample includes binding of the conjugate to sample analyte, to form an analyte-conjugate complex, the reagent composition in the reagent strip includes an anti-analyte antibody immobilized at a detection region in the reagent strip, and the reaction to form a detectable analyte-dependent product includes binding of complex to the immobilized antibody, to localize the detectable reporter in the complex at the detection zone.

3. The cassette of claim 2, wherein said non-immobilized conjugate is a conjugate of an anti-analyte antibody and a detectable reporter selected from the group consisting of metal particles, particles labeled with colored or fluorescent moieties, polymers labeled with colored of fluorescent moieties, particles, and colored or fluorescent molecules.

4. The cassette of claim 3, for use in detecting C-reactive protein analyte in a blood sample, wherein the anti-analyte antibody in the non-immobilized conjugate in the reagent reservoir, and the immobilized anti-analyte antibody in the reagent strip are antibodies specific against a common epitope in C-reactive protein.

5. The cassette of claim 1, wherein said support includes a window through which a detectable reaction at the detection zone in the reagent strip be viewed.

6. The cassette of claim 4, wherein the detection zone in the reagent strip is covered by a reflective film at the strip's surface facing away from said window, such that flow of sample liquid through the detection zone produces a first change in reflectance measurable through the window, and the presence of analyte-dependent reaction at the detection zone produces a second change in reflectance measurable through the window.

7. The cassette of claim 1, which further includes an absorbent reservoir carried on said support, downstream of said detection zone, and in fluid-flow communication with said reagent strip, for receiving sample liquid transferred onto the reagent strip.

8. An apparatus for use in detecting an analyte in a liquid body-fluid sample, comprising:
   A) a cassette having
   (a) a cassette body having a sample well for receiving said sample,
   (b) carried on said cassette body, (i) a reagent reservoir containing a first reagent composition effective to react with one or more sample components to form a modified sample, as sample migrates from the sample well into the reservoir,
   (c) a support mounted with respect to said cassette body, for movement toward and away from a transfer position,
   (d) carried on said support, a reagent strip containing a second reagent composition effective to react with the modified sample to form a detectable analyte-dependent product, said support containing a sample-transfer zone which is brought into contact with said reservoir, when the support is moved to its transfer position, and a detection zone downstream of the transfer zone; and
   (B) a cassette handling instrument having
   (a) a cassette holder into which the cassette is removably placed, during a sample assay,
   (b) an actuator operable to move the support in the cassette toward and away from its sample-transfer position,
   (c) a detector operable to detect an analyte-specific reaction at the detection zone in the reagent strip, and
   (d) a control unit operably connected to the actuator, for controlling the volume and rate of sample transfer from said reagent reservoir to the reagent strip during an assay procedure.

9. The apparatus of claim 8, for detecting a multivalent analyte in a liquid body-fluid sample, wherein the first reagent composition in the reagent reservoir includes a non-immobilized conjugate of an anti-analyte antibody and a detectable reporter group, the reaction to form a modified sample includes binding of the conjugate to sample analyte, to form an analyte-conjugate complex, the reagent composition in the reagent strip includes an anti-analyte antibody immobilized at a detection region in the reagent strip, and the reaction to form a detectable analyte-dependent product includes binding of complex to the immobilized antibody, to localize the detectable reporter in the complex at the detection zone.

10. The apparatus of claim 9, wherein said non-immobilized conjugate is a conjugate of an anti-analyte antibody and a detectable reporter selected from the group consisting of metal particles, particles labeled with colored or fluorescent moieties, polymers labeled with colored of fluorescent moieties, particles, and colored or fluorescent molecules.

11. The apparatus of claim 10, for use in detecting C-reactive protein analyte in a blood sample, wherein the anti-analyte antibody in the non-immobilized conjugate in the reagent reservoir, and the immobilized anti-analyte antibody in the reagent strip are antibodies specific against a common epitope in C-reactive protein.

12. The apparatus of claim 8, wherein said support includes a window through which a detectable reaction at the detection zone in the reagent strip be detected by said detector.

13. The apparatus of claim 12, wherein the detection zone in the reagent strip is covered by a reflective film at the strip's surface facing away from said window, such that flow of sample liquid through the detection zone produces a first change in reflectance measurable through the window, and the presence of analyte-dependent reaction at the detection zone produces a second change in reflectance measurable through the window.

14. The apparatus of claim 13, wherein said detector is operable to detect liquid flow through the detection zone, by a first change in measured optical reflectance, and is operable to measure a subsequent analyte-dependent reaction at the detection zone, by a second change in measured optical reflectance.

15. The apparatus of claim 8, wherein said control unit is operable to control the volume and rate of sample transfer from the reagent reservoir to the reagent strip by controlling one or more of (i) the period of sample incubation before sample is first transferred from the reservoir to the reagent strip, (ii) the cycle frequency with which the actuator moves the support toward and away from its transfer position, (iii) the time of contact that the support is held in its transfer position, during each cycle, and (iv) the total number of transfer cycles.

16. The apparatus of claim 15, wherein the control unit is operable to control the rate of sample transfer from said reservoir to the reagent strip by controlling (i) the cycle frequency with which the actuator moves the support toward and away from its transfer position and (ii) the time of contact that the support is held in its transfer position, during each cycle.

17. A method of conducting an assay for a body-fluid analyte comprising:
   introducing a body fluid containing the analyte into an absorbent reservoir containing a first reagent composition effective to react with one or more sample components to form a modified sample;
   repeatedly contacting the reservoir, with such reservoir containing an absorbed body-fluid sample, with a reagent strip containing a second reagent composition effective to react with the modified sample formed in said reservoir to produce a detectable analyte-dependent product; and
   controlling the frequency and duration of said repeated contacting, thereby to control the volume and rate of transfer of sample fluid from the reservoir to the pad.

18. The method of claim 17, wherein said reagent strip is an elongate reagent strip having a sample-transfer zone at which the reservoir makes contact with the strip, and a detection zone located downstream of the transfer zone.

19. The method of claim 18, for detecting a multivalent analyte in a liquid body-fluid sample, wherein the first reagent composition in the absorbent reservoir includes a non-immobilized conjugate of an anti-analyte antibody and a detectable reporter group, the reaction to form a modified sample includes binding of the conjugate to sample analyte, to form an analyte-conjugate complex, the reagent composition in the reagent strip includes an anti-analyte antibody immobilized at a detection region in the reagent strip, and the reaction to form a detectable analyte-dependent product includes binding of complex to the immobilized antibody, to localize the detectable reporter in the complex at the detection zone.

20. The method of claim 19, wherein said non-immobilized conjugate is a conjugate of an anti-analyte antibody and a detectable reporter selected from the group consisting of metal particles, particles labeled with colored or fluorescent moieties, polymers labeled with colored of fluorescent moieties, particles, and colored or fluorescent molecules.

21. The method of claim 20, for use in detecting C-reactive protein analyte in a blood sample, wherein the anti-analyte antibody in the nonimmobilized conjugate in the reagent reservoir, and the immobilized anti-analyte antibody in the reagent strip are antibodies specific against a common epitope in C-reactive protein.

* * * * *